United States Patent [19]

Mader

[11] 4,024,106

[45] May 17, 1977

[54] 2,4-DIHYDROXY-4-PENTADECYL BENZOPHENONE AND COMPOSITIONS CONTAINING THE SAME

[75] Inventor: Roger A. Mader, Stillwater, Minn.

[73] Assignee: Minnesota Mining and Manufacturing Company, St. Paul, Minn.

[22] Filed: Nov. 17, 1975

[21] Appl. No.: 632,363

[52] U.S. Cl. .......................... 260/45.95 F; 260/591; 106/187

[51] Int. Cl.$^2$ ..................... C07C 49/82; C08K 5/13

[58] Field of Search ..... 260/45.95 F, 591, 45.85 B; 106/187

[56] References Cited

UNITED STATES PATENTS

| 2,999,843 | 9/1961 | Porck | 260/45.95 F |
| 3,033,814 | 5/1962 | Tholstrup | 260/45.85 B |
| 3,043,797 | 7/1962 | Addleburg et al. | 260/45.85 B |

OTHER PUBLICATIONS

Photodegradation, Photooxidation and Photostabilization of Polymers – Ranby et al., Sept. 1975; pp. 369 to 374.

Primary Examiner—V. P. Hoke
Attorney, Agent, or Firm—Cruzan Alexander; Donald M. Sell; Richard Francis

[57] ABSTRACT 2,4'-Dihydroxy-4-pentadecyl benzophenone is prepared by mixing in the presence of an acid catalyst equimolar amounts of meta pentadecyl phenol and parahydroxy benzoic acid. Thermoplastic resins, normally susceptible to degradation upon prolonged exposure to ultraviolet light, become resistant to such degradation when a small amount of 2,4'-dihydroxy-4-pentadecyl benzophenone is blended therein.

11 Claims, No Drawings

2,4-DIHYDROXY-4-PENTADECYL BENZOPHENONE AND COMPOSITIONS CONTAINING THE SAME

This invention relates to 2,4'-dihydroxy-4-pentadecyl benzophenone. In another aspect, the invention relates to thermoplastic resin compositions which include this chemical compound to inhibit ultraviolet light degradation.

BACKGROUND OF THE INVENTION

It is well known that chemical reactions may occur when certain plastic materials are exposed to sunlight or indoor fluorescent lighting due to the presence of ultraviolet light rays in these light sources. Such exposure causes visible discoloration, embrittlement, loss of tensile strength, or other undesirable changes in these plastic materials. Such occurrences are much more pronounced when the plastic is in the form of a thin coating or film rather than a heavier structure such as a bottle or tube which provide a greater bulk for the light rays to penetrate.

One well known method of inhibiting the harmful affects of ultraviolet light exposure is to incorporate opaque pigments into the plastic material. Although extremely effective in reducing degradation induced by ultraviolet light, these pigments render the article opaque to visible light, an unwanted situation where transparency of the article is important.

The preferred ultraviolet light inhibiting additives for normally transparent thermoplastic compositions are organic compounds which can be blended with the thermoplastic material and will inhibit the harmful effect of ultraviolet light exposure without interfering with transparency. A number of organic compounds are known to inhibit degradation of many plastic materials or resinous compositions but these are generally very selective and will not be compatible with a wide variety of plastic materials. For example, 2,4-dihydroxy benzophenone is known to be a useful ultraviolet light inhibitor for cellulose resins, epoxide resins, polyester resins and polystyrene but it is not recommended for use in acrylonitrile/butadiene/styrene polymers, polyethylene, polypropylene and vinyl polymers.

Other considerations in selecting an ultraviolet light inhibiting additive for a particular polymeric material or resin depend on economic factors and technical considerations which may not be related to ultraviolet light absorbents. The ultraviolet light inhibiting additive compound should have relatively high solubility in the polymeric material to which it is added and a low rate of loss from the material through exudation, volatilization, leaching or other means. The compound should have no chemical reactivity with the plastic material, other additives which may be present in the plastic material, or catalyst residues or other contaminants typically found in the plastic material. Preferably, the additive compound should have little or no color and provide little or no color to the plastic material to which it is added and such a condition should remain even upon exposure to heat or light. The additive compound should have low toxicity and should not induce skin reactions or other adverse effects when it is placed into contact with hands or other parts of the body. The additive compound should be easy to compound with the polymeric material and should also have the lowest possible cost consistent with desired performance for the composition.

In some instances some of these factors are unimportant, depending upon the intended use of the polymeric material with which the additive is blended. For example, in a formulation of polyethylene for ultimate use as a tarpaulin, color and toxicity are of minor importance, and high ultraviolet light absorbing efficiency and performance are of major importance. In the case of polystyrene light fixture diffusers, low initial color and freedom from discoloration upon exposure to light are prime considerations.

A wide variety of ultraviolet light absorbers is presently available to meet, in a limited degree, each of these requirements. A listing of such ultraviolet light absorbers may be found, for example, in the article by C. H. Fuchsman and F. R. Hansen commencing on page 436 of The Modern Plastics Encyclopedia published by McGraw Hill Inc., New York, New York (1972) and in the chart of ultraviolet light absorbing materials found on pages 488–489 of the same publication. Further information on such materials is provided in an article by R. F. Jackson commencing on page 264 of Modern Plastics Encyclopedia, published by McGraw Hill Inc., New York, New York (1974/1975).

BACKGROUND OF THE PRIOR ART

The most common ultraviolet light inhibiting additives are the substituted 2-hydroxy benzophenones. These compounds have proven useful for a relatively wide albeit somewhat limited variety of polymers. Among the most widely used substituted 2-hydroxy benzophenones are 2,4-dihydroxy benzophenone, 2-hydroxy-4-(octyloxy)benzophenone, and 4-(dodecyloxy)-2-hydroxy benzophenone. U.S. Pat. No. 2,999,843 discloses stabilization of polyolefin compositions with 2-hydroxy-4-pentadecyl benzophenone. Volume 14 of Encyclopedia of Polymer Science and Technology, Kirk Orthmer, the article entitled *Ultraviolet-Radiation Absorbers*, pages 125–148 John Wiley and Sons, Inc., New York (1971) discloses a number of substituted 2-hydroxy benzophenone ultraviolet light stabilizer additives and their commercial designations.

The alkyl- or alkoxy-substituted 2-hydroxy benzophenones have been found to be generally compatible with more polar polymers such as polystyrene, vinyl polymers, polyesters and cellulose resins, although generally unsuitable for the non-polar polymers such as polyolefins. 2,4'-dihydroxy benzophenone is a highly polar compound which is useful as an ultraviolet light absorber in the more polar polymers. 2-hydroxy benzophenone substituted with long chain length alkyl groups such as 2-hydroxy-4-pentadecyl benzophenone (described in U.S. Pat. No. 2,999,843) provides increased solubility in non-polar polymers such as polyethylene and polypropylene but results in lower compatibility with the highly polar polymers. Most of the prior art 2-hydroxy benzophenones and substituted 2-hydroxy benzophenones have a relatively high volatility, resulting in considerable loss of these materials during processing such as molding or extrusion which requires temperatures near or above the melting point of the plastics. Many of the substituted monohydroxy benzophenones have a limited or narrow absorption band in the ultraviolet light spectrum, providing limited protection or requiring the addition of other compounds which absorb in the remaining ultraviolet wave lengths.

SUMMARY OF THE PRESENT INVENTION

The present invention provides the new chemical compound 2,4'-dihydroxy-4-pentadecyl benzophenone. This compound is a unique ultraviolet light absorbing material which, quite unexpectedly, is compatible with any of a wide variety of plastic materials. This new compound has a light yellow color and has excellent ultraviolet light absorbing properties. The compound of the invention also has low volatility, making it useful in conventional plastic processing equipment without reducing its effective quantity, and it is made from inexpensive commercially available materials.

This new compound may be prepared by the acid catalyzed condensation of parahydroxy benzoic acid with meta pentadecyl phenol, preferably in about equimolar amounts. The reaction is preferably carried out in the absence of atmospheric moisture.

It is well recognized that compatibility of substituted 2-hydroxy benzophenones with various polymeric materials, whether they be polar or non-polar, is a sensitive function of molecular structure and is generally not predictable. 2,4'-dihydroxy benzophenone is a highly polar material which is compatible with polar polymers and is desirable because it has a broad absorption spectrum in the ultraviolet, although this compound is somewhat volatile. This material is generally poorly compatible with non-polar polymers such as polyethylene and polypropylene, however. Adding a long alkyl group to 2-hydroxy benzophenone (e.g., 2-hydroxy-4-pentadecyl benzophenone which is described in U.S. Pat. No. 2,999,843) tends to counteract the polar nature of this compound, making it more compatible and thus useful as an ultraviolet light inhibitor in non-polar polymers such as polyethylene and polypropylene. Because of the highly polar nature of the more desirable broad band inhibitor, 2,4'-dihydroxy benzophenone, it is unpredictable as to whether or not the addition thereon of a long chain alkyl group would produce a compound which would be sufficiently compatible in non-polar polymers such as polypropylene. In fact, when applicant produced such a compound, i.e., the compound of the invention, it had virtually no solubility at room temperature in non-polar solvents such as hexane and tetrapropylene, indicating it would likewise be insoluble in higher molecular weight non-polar polymeric materials such as polypropylene. Quite unexpectedly and contrary to such initial findings, this compound was found to be quite compatible with non-polar polymers including polypropylene. In fact, this compound was discovered to be compatible with any one of a wide variety of thermoplastic polymeric materials.

DETAILED DESCRIPTION OF THE INVENTION

The preferred equipment for carrying out the reaction to produce the compound of the invention includes a vessel which can be closed to the surrounding ambient atmosphere and is made of a material which is inert to the reactants and the catalyst. The vessel should have fittings to accommodate a stirrer, condenser, and thermometer and be equipped with a drain and an inlet for a purging gas. Means for heating and cooling the vessel should also be provided. A suitable vessel is made of copper-nickel alloy known as "Monel".

The reaction is carried out in the presence of a Friedel-Crafts catalyst such as anhydrous hydrogen fluoride. The amount of catalyst required, functionally stated, is that amount at least sufficient to cause a reaction to go to completion. In the case of hydrogen fluoride a large excess is used, since the material also serves as a reaction medium.

The reaction vessel is sealed, the air replaced by a dry atmosphere and the reactants charged in single batches, the order being unimportant. Thereafter, the vessel is sealed, and the contents cooled preferably to about 0° C whereupon the catalyst is added. Thereafter, the vessel is slowly warmed to a temperature and for a time sufficient to allow the reactants to react, preferably while agitating the reactants. A preferred reaction time is from about 4 to 8 hours but this will vary depending upon the temperature. At higher temperatures, less time will be required. The preferred reaction temperature is from about 20° C to 100° C, most preferably about 70° C.

The starting materials employed to produce the compound of the invention are well known materials which are commercially available. Meta pentadecyl phenol is described in U.S. Pat. No. 3,284,369. Parahydroxy benzoic acid is also well known.

As previously mentioned, the new compound of the invention blends quite readily with any of a wide variety of polymeric materials in quantities sufficient to inhibit degradation of these materials by exposure to ultraviolet light. The amount of 2,4'-dihydroxy-4-pentadecyl benzophenone required to have this effect, functionally stated, is the minimum amount for the thickness of the particular article into which the plastic material is formed to prevent ultraviolet light degradation. The amount should not be so great as to interfere with the physical properties of the plastic material, e.g., transparency or physical strength. Typically, the amount of 2,4'-dihydroxy-4-pentadecyl benzophenone in such polymeric materials will be on the order of 0.01 to about 10 (generally 0.05 to 2.5) percent of the total weight of the composition, preferably 0.1–1 percent by weight.

The compound of the invention is compatible with thermoplastic materials such as polyolefins, for example polyethylene and polypropylene, polyesters such as polyethylene terephthalate, cellulose resins, polyacrylates, epoxide resins, polystyrene, poly(vinyl chloride), poly(vinylidene chloride) and others.

While this material is of the greatest value in transparent polymeric materials, the compositions to which it may be added may also include such conventional additives as plasticizers, pigments, dyes and reinforcing filler materials and the like which may reduce the transparency of the composition. 2,4'-dihydroxy-4-pentadecyl benzophenone is generally compatible with substantially all materials known for such purposes.

The compound of the invention may be added to the polymeric resinous material by any of a wide variety of known methods. These methods include dry blending particulate polymeric material and the compound of the invention, melt mixing the compounds either in an extruder or in a suitable mixing device, or by blending a solvent solution of this material with the polymeric material. For the latter purpose methylene chloride has been found to be an excellent solvent.

The invention is illustrated by the following nonlimiting examples, wherein all parts are by weight unless otherwise specified.

EXAMPLE 1

Parahydroxy benzoic acid (10.3 parts) and 22.8 parts of meta-pentadecyl phenol were separately charged into a "Monel" reaction vessel equipped with stirrer, condenser, drain, and facilities for heating and cooling. The vessel was sealed, the air replaced by dry nitrogen, and the vessel contents cooled to about 0° C, whereupon 45 parts substantially anhydrous hydrogen fluoride was added. Thereafter the vessel was slowly warmed to 75° C with stirring and held at this temperature with continued stirring for approximately six hours to complete the reaction. After this time, the contents of the vessel were cooled to about 25° C and the excess hydrogen fluoride vented. To the residue contained in the flask was added, with care, 100 parts of deionized water and this mixture was vigorously stirred for 30 minutes, causing a moderate exotherm which was maintained at 70° C. The reaction vessel was then cooled to about room temperature and substantially all of the water was removed with a filter stick, leaving a solid residue which was then dissolved in 25 parts of ethyl acetate. A mixture of 4 parts isopropyl alcohol and 16 parts deionized water was then added to the ethyl acetate solution and the resultant mixture vigorously agitated for 15 minutes. After this time, the aqueous and organic liquid phases were permitted to separate and the aqueous phase removed and discarded. The organic phase was washed twice more with the same amount of the mixture of isopropyl alcohol and deionized water. After washing, the reaction vessel contents were heated to distill the ethyl acetate and upon substantially complete removal, the reaction vessel contents were cooled to about 60° C and 50 parts hexane added. This mixture was permitted to cool for about 3 hours until the temperature reached 25° C when it was filtered and the filter cake washed with an additional 10 parts of hexane. The resultant residue was air dried to remove residual hexane and leave the desired chemical compound.

Elemental analysis of the resultant compound revealed 79.6% carbon and 9.5% hydrogen as compared with a theoretical value of 79.2% carbon and 9.4% hydrogen for 2,4'-dihydroxy-4-pentadecyl benzophenone. Spectral analysis by infrared, ultraviolet and nuclear magnetic resonance confirmed that this compound was 2,4'-dihydroxy-4-pentadecyl benzophenone. The product had a melting point of 79°–80° C.

EXAMPLE 2

Samples of polypropylene and polyethylene containing respectively 2% and 1% by weight of 2,4'-dihydroxy-4-pentadecyl benzophenone according to the invention were prepared. A sufficient quantity of a 10% by weight solution of 2,4'-dihydroxy-4-pentadecyl benzophenone in methylene chloride was dry blended with finely divided polyolefin. Portions of the blends were then pressed in a platen press at 240° C to produce a film having a thickness of about 1 millimeter. These films were as transparent as unstabilized polyolefin film prepared in the same manner. The films containing 2,4'-dihydroxy pentadecyl benzophenone absorbed ultraviolet light.

EXAMPLE 3

A 1 mm thick polypropylene sample containing 2% 2,4'-dihydroxy-4-pentadecyl benzophenone was exposed for 72 hours to a 275 watt sunlamp at a distance of 25 cm in air at 50° C. A 1 mm thick control polypropylene film without this additive was exposed in a like manner. The tensile strength of these exposed samples and an unexposed polypropylene control film containing no additive was determined by using an "Instron" tensile testing device. Results in kilonewtons per square meter ($kN/m^2$) are shown below.

| Polypropylene Sample | Tensile Strength ($kN/m^2$) |
| --- | --- |
| no additive, unexposed | 80 |
| 2% additive, exposed | 80 |
| no additive, exposed | 11 |

These results reveal that polypropylene film containing the additive according to the invention sustained no loss in tensile strength upon exposure to ultraviolet light while polypropylene film not containing this additive sustained an 85% decrease in tensile strength.

EXAMPLE 4

Samples of polypropylene containing 0.05 to 2.5% by weight of 2,4'-dihydroxy-4-pentadecyl benzophenone were prepared by dry blending finely divided polypropylene with the desired amount of powdered ultraviolet absorber and extruding about 200 grams of each blend through a 1 inch extruder at a 16 to 1 compression ratio and a 230° C die temperature. No release of volatile absorber was observed during extrusion. The 0.01 mm film was in each case essentially transparent and resistant to degradation by ultraviolet light.

EXAMPLE 5

The volatility of the compound according to the invention was determined by thermogravimetric analysis. This method involves placing a weighed amount of the material under investigation on a balance designed to be heated to successively higher temperatures while simultaneously determining the residual weight. In such an experiment, the 2,4'-dihydroxy-4-pentadecyl benzophenone, heated at a rate of 40° C per minute, showed a weight loss of 1% at about 300° C, 2% at about 310° C and 5% at 325° C. By contrast, 2-hydroxy-4-pentadecyl benzophenone lost about 1% of its weight at only 250° C, 2% at 270° C and 5% at 290° C. Additionally and in contrast, a common commercial ultraviolet light absorber, 2,4-dihydroxy benzophenone, showed a loss of 1% at only 190° C, obviously revealing the absorber of the invention to be far superior when utilized as an additive in thermoplastic compositions which require relatively high processing temperatures.

What is claimed is:

1. A composition comprising a thermoplastic resin which is normally subject to degradation upon prolonged exposure to ultraviolet light rays and a small but effective amount of 2,4'-dihydroxy-4-pentadecyl benzophenone to inhibit said degradation.

2. The composition of claim 1 wherein said thermoplastic resin is selected from the group consisting of cellulose resin, epoxide resin, polyester, polypropylene, polyethylene, polystyrene, poly(vinylchloride) and poly(vinylidene chloride).

3. A composition comprising from about 97.5 to about 99.95 percent by weight of a thermoplastic resin which is normally subject to degradation upon prolonged exposure to ultraviolet light rays and correspondingly from about 2.5 to about 0.05 percent by weight 2,4'-dihydroxy-4-pentadecyl benzophenone.

4. The composition of claim 3 wherein said thermoplastic resin is selected from the group consisting of cellulose resin, epoxide resin, polyester, polypropylene, polyethylene, polystyrene, poly(vinylchloride) and poly(vinylidene chloride).

5. A polypropylene composition containing blended therein from about 0.05% to about 2.5% by weight 2,4'-dihydroxy-4-pentadecyl benzophenone.

6. A shaped article comprising a self-supporting shaped structure formed of the composition of claim 1.

7. Polypropylene film having dispersed therein a small but effective amount of 2,4'-dihydroxy-4-pentadecyl benzophenone sufficient to inhibit ultraviolet light degradation of the polypropylene contained in the film.

8. The polypropylene film of claim 7 wherein said 2,4'-dihydroxy-4-pentadecyl benzophenone comprises from about 0.05% to about 2.5% of the weight of said film.

9. A method of inhibiting ultraviolet light degradation of thermoplastic resin comprising homogeneously blending into said resin a small but effective amount of 2,4'-dihydroxy-4-pentadecyl benzophenone sufficient to inhibit ultraviolet light degradation.

10. The method of claim 9 wherein said small but effective amount is from about 0.05% to about 2.5% by weight 2,4'-dihydroxy-4-pentadecyl benzophenone.

11. 2,4'-dihydroxy-4-pentadecyl benzophenone.

* * * * *